United States Patent
Nunes et al.

(10) Patent No.: US 10,139,268 B2
(45) Date of Patent: Nov. 27, 2018

(54) SYSTEMS AND METHODS FOR MULTIPLE-CODE CONTINUOUS-WAVE DISTRIBUTED ACOUSTIC SENSING

(71) Applicant: Halliburton Energy Services, Inc., Houston, TX (US)

(72) Inventors: Leonardo de Oliveira Nunes, Rio de Janeiro (BR); Christopher Lee Stokely, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 211 days.

(21) Appl. No.: 15/108,760

(22) PCT Filed: Jan. 21, 2014

(86) PCT No.: PCT/US2014/012284
§ 371 (c)(1),
(2) Date: Jun. 28, 2016

(87) PCT Pub. No.: WO2015/112116
PCT Pub. Date: Jul. 30, 2015

(65) Prior Publication Data
US 2016/0320232 A1 Nov. 3, 2016

(51) Int. Cl.
| | |
|---|---|
| *E21B 43/26* | (2006.01) |
| *E21B 47/09* | (2012.01) |
| *G01D 5/353* | (2006.01) |
| *G01V 1/52* | (2006.01) |
| *G01N 29/24* | (2006.01) |
| *G01M 3/24* | (2006.01) |
| *G01H 9/00* | (2006.01) |
| *E21B 43/267* | (2006.01) |

(52) U.S. Cl.
CPC .............. *G01H 9/004* (2013.01); *E21B 43/26* (2013.01); *E21B 43/267* (2013.01); *E21B 47/091* (2013.01); *G01D 5/35361* (2013.01); *G01M 3/24* (2013.01); *G01N 29/2418* (2013.01); *G01V 1/52* (2013.01); *G01V 2210/1429* (2013.01)

(58) Field of Classification Search
CPC ..... G01M 3/24; G01N 29/2418; G01H 9/004; G01D 5/35361; G01V 1/52; G01V 2210/1429; E21B 43/26; E21B 43/267; E21B 47/091
USPC ......................................... 73/152.5
See application file for complete search history.

(56) References Cited

U.S. PATENT DOCUMENTS

| | | | |
|---|---|---|---|
| 5,000,568 | A | 3/1991 | Trutna et al. |
| 5,194,847 | A | 3/1993 | Taylor et al. |
| 5,353,627 | A | 10/1994 | Diatschenko et al. |
| 5,635,829 | A | 6/1997 | Hamada |

(Continued)

FOREIGN PATENT DOCUMENTS

| | | |
|---|---|---|
| JP | 2013079906 A | 5/2013 |
| JP | 2013181789 A | 9/2013 |
| KR | 1020130081062 A | 7/2013 |

*Primary Examiner* — J M Saint Surin
(74) *Attorney, Agent, or Firm* — Gilliam IP PLLC

(57) ABSTRACT

A method and device for monitoring oil field operations with a fiber optic distributed acoustic sensor (DAS) that uses a continuous-wave fiber optic distributed acoustic sensor with a very small spatial sampling while being able to sense acoustic events that have a large bandwidth by employing a demodulation/decoding method utilizing multiple spread-spectrum codes.

21 Claims, 4 Drawing Sheets

(56) References Cited

U.S. PATENT DOCUMENTS

| | | | |
|---|---|---|---|
| 5,686,986 A | 11/1997 | Li et al. | |
| 6,043,921 A * | 3/2000 | Payton | H04B 10/60 |
| | | | 398/1 |
| 6,173,091 B1 | 9/2001 | Reich | |
| 6,285,806 B1 | 9/2001 | Kersey et al. | |
| 7,268,863 B2 | 9/2007 | Payton | |
| 7,271,884 B2 | 9/2007 | Payton | |
| 7,274,441 B2 | 9/2007 | Payton | |
| 7,946,341 B2 | 5/2011 | Hartog et al. | |
| 9,733,120 B2 * | 8/2017 | Stokely | G01H 9/004 |
| 2006/0028636 A1 | 2/2006 | Payton | |
| 2006/0066839 A1 | 3/2006 | Payton | |
| 2009/0114386 A1 * | 5/2009 | Hartog | E21B 43/26 |
| | | | 166/250.08 |
| 2012/0060610 A1 * | 3/2012 | Oaks | A61B 8/4444 |
| | | | 73/632 |
| 2012/0287749 A1 * | 11/2012 | Kutlik | G01H 3/125 |
| | | | 367/7 |
| 2013/0092371 A1 * | 4/2013 | Hartog | E21B 47/06 |
| | | | 166/250.01 |
| 2014/0139841 A1 * | 5/2014 | Koste | G01D 5/35358 |
| | | | 356/477 |

\* cited by examiner

SYSTEMS AND METHODS FOR MULTIPLE-CODE CONTINUOUS-WAVE DISTRIBUTED ACOUSTIC SENSING

CROSS-REFERENCE TO RELATED APPLICATIONS

Not applicable.

BACKGROUND

Fiber-optic sensors are increasingly being used as devices for sensing some quantity, typically temperature or mechanical strain, but sometimes also displacements, vibrations, pressure, acceleration, rotations, or concentrations of chemical species. The general principle of such devices is that light from a laser is sent through an optical fiber and there experiences subtle changes of its parameters either in the fiber itself or in one or several point-location sensing fiber Bragg gratings and then reaches a detector arrangement which measures these changes.

In particular a growing application field is the use of fiber optic sensing system for acoustic sensing, especially Distributed Acoustic Sensing (DAS). DAS optical fibers can be deployed into almost any region of interest and used to monitor for occurrences that generate acoustic perturbations. DAS is quickly becoming recognized as a powerful tool for remote sensing in oil and gas operations. The list of existing and potential applications in remote sensing for this new technology continues to grow and includes not only downhole or subsurface applications but other applications in which acoustic perturbations are of interest, such as subsea umbilical's and risers, and in the security field for perimeter security. Basically any structure can be monitored for acoustic perturbations in this way. Traditionally, DAS applications in the subsurface environment use pulsed electromagnetic waves to interrogate a fiber optic cable for sensing acoustic and vibration phenomena in an oil well, or reservoir. This type of sensor is sometimes referred to as a time-domain coherent optical reflectometer and utilizes a technique called time division multiplexing. In summary, a short electromagnetic coherent pulse (usually in the infrared) is injected into one end of a fiber optic. Pulses are back reflected or backscattered via Rayleigh scattering along a continuum of virtual reflectors in the fiber and these pulses are analyzed using interferometric techniques. A phase of the returned light is measured that is related to the local stretch in the fiber optic during its exposure to an acoustic pressure wave. The optical phase ideally will vary linearly with the acoustic pressure wave. Once a light pulse is injected, a period of time should be surpassed before injecting another pulse of light. This amount of time is twice the transit time of light from the injection location to the end of the fiber. This is done to ensure there is no light in the fiber when another pulse of light is injected. The pulse repetition frequency of the DAS is the reciprocal of the wait time between light injections. Half of the pulse repetition frequency is the well-known Nyquist frequency, which is the maximum acoustic bandwidth available for monitoring.

As the business intensity grows in the worldwide campaign to find and produce more oil there is increasing need to better monitor subsurface oil field operations using more sophisticated acoustic monitoring. In particular there are increasingly applications in which there is a need for detecting much higher frequency and higher bandwidth acoustic signals than that available with time division multiplexing alone. Examples include an increasing interest in listening for sand flow, high bandwidth telemetry, listening for proppant in hydraulic fracturing operations, measuring fluid flow by acoustic signatures (particularly with active ultrasonic flow monitoring systems), monitoring flow regimes, listening for wellbore leaks (often high frequency), listening for cavitation in flow, listening for plug leaks or inter-zone leaks, monitoring vortex shedding, and wireline sonic logging. These applications require a sensitive listening device with an increased audio bandwidth and an improved signal-to-noise ratio.

The technical approach to be described in this application does not rely on the pulsed laser time division multiplexing described above.

DETAILED DESCRIPTION

Figure 1:
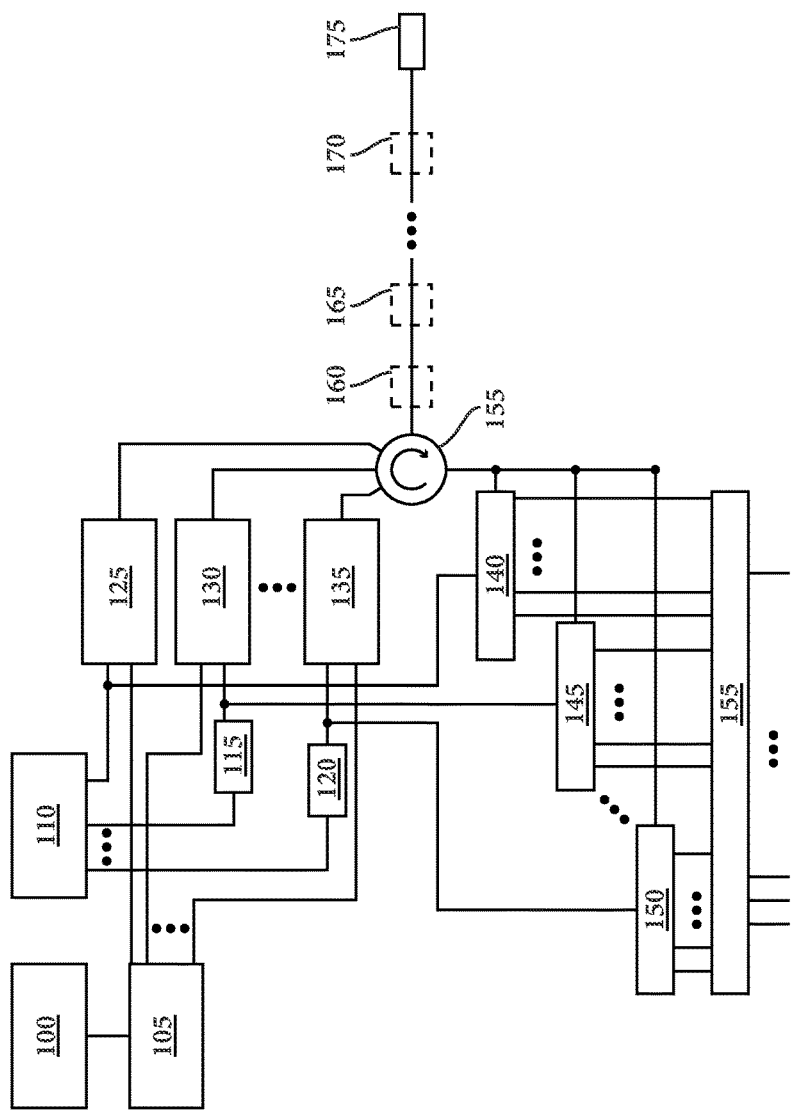
FIG. 1 is an overview schematic of the system proposed by this disclosure.

In the following detailed description, reference is made that illustrate embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken in a limited sense, and the scope of the disclosure is defined only by the appended claims.

Traditional distributed acoustic sensing is analogous in some ways to radar techniques used in traditional pulse-echo ranging techniques. A short electromagnetic coherent pulse (usually in the infrared) is injected into one end of a fiber optic. Pulses are back reflected via Rayleigh scattering along a continuum of virtual reflectors in the fiber and these pulses are analyzed using interferometric techniques. A phase is measured that is related to the local stretch in the fiber optic during its exposure to an acoustic pressure wave. The phase ideally will vary linearly with the acoustic pressure wave. In a sense, a conventional distributed acoustic sensor acts as radar with a virtual continuum of reflections from Rayleigh scattering along the fiber, similar to radar measurements of extended bodies such as rain clouds.

An alternative to utilizing traditional pulsed ranging measurements is spread spectrum-ranging methods. Some spread spectrum modulation techniques make use of multiplexing and de-multiplexing methods commonly grouped into a technology known as code division multiplexing. This method consists of mixing or modulating a coherent (near) single frequency signal with a pseudo random signal code that has a broad spectrum relative to the signal being sensed. We will describe solutions employing bipolar codes having +1 and −1 values. The sequence does not allow zeroes since that would result in a signal chopped in time. The receiver demodulates or recovers the original signal with a binary code that is uniquely paired (or nearly so) with the original binary code. Each code sequence modulates the coherent signal for short period of time and is generally immediately followed by another code sequence modulation, followed by another, and so on, with requirements known to those skilled in the art.

Each of the reflected signals occupies a unique time-delay slot or bin. And by delaying and multiplying the code sequence and multiplying it by the received signal, we can recover the frequency-modulated signal. A master or carrier wave is modulated by a single code sequence and delayed by the appropriate time interval specific to a particular signal. All such signals are combined by the action of the fiber optic and the transmitted signal consists of a continuous wave pulse that is multiplied by a single coding sequence and transmitted as a composite optical signal to a receiver where these are collected and photo detected. By filtering the photo detected composite optical signal with the master or reference carrier wave, each individual optical signal is sorted or de-multiplexed into separate electronic signal channels.

The phase of the de-multiplexed signal can then be extracted by a frequency modulation (FM) demodulation scheme.

In conventional time-domain reflectometry using fiber optic cables or other mediums such as glass, air, water, etc. over lengths typical of wellbores, the length of the fiber optic cable limits the maximum detectable acoustic frequency. For example, a 10 km fiber optic cable has a maximum acoustic bandwidth of 5 kHz. Time-domain reflectometry methods do not sample the optical medium fast enough to detect tens or hundreds of kilohertz bandwidth variations in the medium. There is a considerable range of events that occur in a well that produce acoustic perturbations above the 5 kHz range. Multiple fluids and phases (gas bubbles, solids, and some liquid mixtures) may produce recognizable acoustic signatures. The extension of reflectometry into much higher frequencies by the use of the spread spectrum technique of this disclosure can open acoustic monitoring into a realm of new application space—to include an increasing interest in listening for sand flow, high bandwidth telemetry, listening for proppant in hydraulic fracturing operations, measuring fluid flow by acoustic signatures (particularly with active ultrasonic flow monitoring systems), monitoring flow regimes, listening for wellbore leaks (often high frequency), listening for cavitation in flow, listening for plug leaks or inter-zone leaks, monitoring vortex shedding, and wireline sonic logging.

These applications require a sensitive listening device with an increased audio bandwidth and an improved signal-to-noise ratio. Both are characteristics of spread spectrum techniques. It is anticipated that all of these applications can be addressed with the system and method described herein.

The approach also relates to fiber optic sensors and optical sensors generally. A fiber optic sensor array is typically time-domain multiplexed by the time-of-transversal of an interrogation light wave to each sensor and back to a common optical collection and detection point In the technology to be described the continuous wave output of a long coherence length phase-stable infrared laser is modulated with pseudo-random binary code sequences. This is the spread spectrum modulation of a laser using special binary codes. These binary code sequences consist however of ones and negative ones instead of ones and zeros.

The construction or selection of a suitable binary code sequence, or sets of sequences, is not trivial. To guarantee efficient spread-spectrum communications, the pseudorandom number sequences must respect certain rules, such as length, auto-correlation, cross-correlation, orthogonality, correlation side lobe behavior, and bits balancing. The more popular pseudorandom number sequences have names such as Barker, M-Sequence, Gold, Hadamard-Walsh, etc.

Good code sequences for this application have a high, narrow auto-correlation peak, when exactly lined up, which minimizes false synchronization. Auto-correlation is the same as cross-correlation, except with auto-correlation the code is compared against itself, with a relative shift of one chip at a time. With cross-correlation the code sequence is compared against another code sequence with a relative shift of one chip at a time.

In a previously filed application (PCT/US13/54588) the use of auto-correlation codes was the key approach. In other words, the only property of the code used was the fact that, when the code is multiplied by itself, the result is one when the two versions of the code are time-aligned and a small noise-like signal when they are not time-aligned. The auto-correlation function of the code informs us of how much time-delay we can impose on the code before the product becomes noise-like. The more impulsive the auto-correlation signal, the smaller the delay we need to have a noise-like signal.

In this application the additional requirement that was not covered in that application is the cross-correlation properties of the code.

In this disclosure we will describe how we can enable a continuous-wave fiber optic distributed acoustic sensor with a very small spatial sampling while being able to sense acoustic events that have a large bandwidth by employing a demodulation/decoding method utilizing multiple spread-spectrum codes and their cross-correlation properties.

For this, a coherent continuous wave signal is sent down a fiber optical cable and its reflections are recorded. The wave being transmitted can be mathematically described as:

$$E(t) = \sum_{a=1}^{A} c_a(t)\cos(\omega_a t)$$

where $c_a(t)$ is the a-th spreading function and $\omega_a$ is its corresponding angular frequency. It will be described later that by using several codes and frequencies in the interrogating signal, it will be possible to increase the number of regions of the fiber being sensed while increasing the signal-to-noise ratio of the acoustic signal.

It will be assumed that a backscattered signal, composed of the integral of the reflected signals at every position of the fiber optic cable, will go through either a homodyne or heterodyne demodulation process and decoder. Mathematically, the demodulator/decoder will perform the following mathematical calculation, where the output will be associated with a single location of the fiber optic cable:

$$b_{i,j}(t)=[E(t)c_j(t-2c_L^{-1}z_i)\cos((\omega_j+\Delta\omega)t)]*h(t)$$

where the symbol * represents convolution and each $b_{i,j}(t)$ is associated to the i-th region of the fiber being sensed with the j-th carrier frequency/code combination. The function h(t) is a time-domain filter responsible for selecting only the information related to the chosen code and carrier frequency. It should be a filter with bandwidth equal to that of the frequency-modulated acoustic signal and be centered around a frequency equal to $\Delta\omega$. In the case of a homodyne demodulation, $\Delta\omega=0$ and filter h(t) becomes a low-pass filter.

The demodulated signal $b_{i,j}(t)$ is related to the acoustic pressure signal by the following relationship $$b_{i,j}(t) \approx \cos(\Delta\omega t - 2\omega_j c_L^{-1} \hat{z}(t, z_i))$$

with $$\hat{z}(t, z_i) = z_i + \mu \int_0^{z_i} p(t, x) dx$$

where $p(t,x)$ is the pressure wave, $\mu$ is a constant relating pressure to strain, and z is the position associated with elongation of the fiber from the pressure wave. Looking at the equation above it is possible to see that the recovered signal is a cosine carrying the information of the pressure wave for the whole fiber up to a determined position. Hence, in order to extract the pressure information for each region of the fiber, the phase of the signal must be extracted for each position and then the differential phase (related to the integral of the pressure wave in two adjacent positions) calculated.

Code Requirements

The choice of the code and its properties has been covered in a previous PCT filing (PCT/US13/54588). The only other requirement for the codes that were not covered previously is for their cross-correlation properties. This property demands that for two different coding sequences $c_a(t)$ and $c_b(t)$, the following expression is valid $$R_{a,b}(t) = \int c_a(t) c_b(t+\tau) d\tau \approx 0.$$

Also, it will be assumed that all the codes are binary (only assume values −1 and +1, i.e., bipolar), even though different codes can be employed. All codes will be assumed to have a bandwidth of $\sigma_c$ and have a period such that it is able to sense a region of the fiber with length equal to $\Delta_z$ meters. Several families of codes approximate the desired characteristic above. Considering the auto-correlation properties also demanded from the codes, a preferred code family would be Maximal Length Sequences (M-Sequences). It should be noted, however, that the proposal described herein can work with other bipolar coding sequences and also with non-binary pseudo-random noise sequences, with little adjustments performed in the decoding scheme.

In this disclosure, focus will be given in how to adapt the chosen codes and laser frequencies so that the signal can be sensed at different positions and with lower signal-to-noise ratio. Each technique will be described separately.

Code Adaptation

This approach consists of the use of several pseudo-random sequences (codes) to sense the acoustic signal at a given region of the fiber. The multiple codes can be used to sense the same region of the fiber, in this case facilitating a notable improvement in the phase estimation process as well as reducing the signal-to-noise ratio that can be employed to accurately sense different regions of the fiber.

If the same region of the fiber is to be sensed by multiple codes, the codes must be generated with the same period and have all the same phase. That is, they must be generated by the same clock and the transitions between different values for each code must happen synchronously. If this scheme is used, then the signals sensed by each coding sequence are such that $z_i$ is the same for all codes. Considering that A codes are available, A signals for each position are extracted.

The codes can also be employed to sense different regions of fiber. This can be accomplished by delaying each code relative to each other, so that each code has the same period but with a slightly different phase. By generating each code so that $$c_j(t) = c_j\left(t + \frac{j\Delta_z}{A}\right), j = 0, 1, \ldots, A-1$$

where the phase of the pressure signal associated with the signal sensed by each code at position j is:

$$\hat{z}(t, z_i) = z_i + \mu \int_0^{z_i} p(t, x) dx, \text{ for } j = 0$$

$$\hat{z}(t, z_i) = z_i + \mu \int_0^{z_i + \frac{\Delta_z}{A}} p(t, x) dx, \text{ for } j = 1$$

$$\hat{z}(t, z_i) = z_i + \mu \int_0^{z_i + \frac{2\Delta_z}{A}} p(t, x) dx, \text{ for } j = 2$$

Hence, a region of length equal to $$\frac{\Delta_z}{A}$$

can be obtained by subtracting the phase signal of two consecutives codes:

$$\int_0^{z_i + \frac{\Delta_z}{A}} p(t, x) dx - \int_0^{z_i} p(t, x) dx = \int_{z_i}^{z_i + \frac{\Delta_z}{A}} p(t, x) dx$$

Optic Signal Frequency Allocation

The frequency $\omega_j$ associated with each code can be chosen to yield a complete separation between the bandwidths of the different codes. In this case, the frequency separation between them should be $$2(\omega_j - \omega_{j-1}) > \frac{\sigma_{FM}}{2} + 2\sigma_c$$

where $\sigma_{FM}$ is the bandwidth of the frequency modulated signal and $\sigma_c$ is the bandwidth of the code. This separation, however, does not need to be respected for the proposed scheme to work. In fact, due to the cross-correlation property of the chosen codes, several allocation strategies between codes and frequencies can be used. For example, each carrier frequency can be shared for up to M codes as long as their cross-correlation is approximately zero.

FIG. 1 illustrates an overview of the proposed system. In the figure an optical source 100 emits a continuous optical signal with a specified angular frequency $\omega_s$. This optical signal is then shifted in frequency with a frequency modulator 105 so that M optical signals are obtained each possibly having a unique frequency. Each i-th optical signal is then modulated through optical modulators 125, 130, 135 by a bipolar pseudorandom coding sequence using code generator 110 that can be delayed with delays 115, 120 relative to a reference coding sequence. Code generator 110 is responsible for generating each pseudorandom code with the adequate code period synchronized in time. The optical signals from the M modulators are then combined in an optical circulator/coupler 155 and sent down a fiber optic cable span into a region of interest where it is back-reflected in regions $R_1$ through $R_N$, represented here by 160,165,170, where N is the number of regions. The fiber ends at 175. The back-reflected signals then pass back through the circulator are then separated and sent down a series of M demodulators, represented here as 140, 145, 150. Each demodulator is responsible for transforming the optical signal into an electronic one through either homodyne or heterodyne detection, de-coding the signal by the appropriate code, and then extracting the phase information. Each phase output of each demodulator is associated with the pressure wave being applied to the fiber optic up to a certain region $R_N$. In order to obtain the pressure wave for a single region N, a phase differencer must be used so that the phase signals sensed by each code from each region can be combined to obtain the pressure signals impinging on determined length of the fiber optical cable. The phase differencer is also responsible for increasing the spatial resolution of each signal by subtracting the phase of the i-th demodulator for the j-th region from the phase output of the z-th code for the same region. Not depicted in the figure is a master clock, responsible for distributing and maintaining a stable clock signal that is available to all described processing steps. Finally a processor (not shown) detects coherent Rayleigh noise generated by the optical fiber span positioned in the region of interest and identifies acoustic perturbations.

Figure 2:
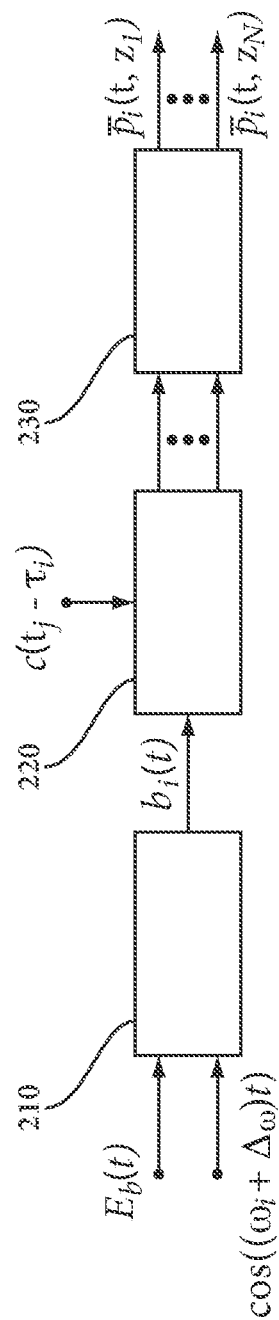
FIG. 2 illustrates a more detailed view of the i-th demodulator of the proposed system.

FIG. 2 shows the three steps used to demodulate and obtain the phase (pressure) signal. As can be seen, the back-reflected signal is first optically demodulated to an electronic signal by either homodyne or heterodyne demodulation 210. The electronic signal is then sent to a decoder or de-spreader 220 that is responsible for obtaining a frequency-modulated signal whose phase is related to the pressure wave impinging on the fiber optic cable up to a certain spatial region. The phase information of each signal related to the pressure up to a certain spatial region is then estimated through a frequency/phase demodulator 230. Each output of the phase-demodulator is the integral of the pressure wave impinging on the fiber optic cable up to a certain region of the fiber. In this disclosure, the use of M such demodulators, each for a different spreading code, is proposed. Note that the functionality shown in FIG. 2 could be implemented as stand-alone circuits or in software code. Either approach is anticipated in this disclosure.

Figure 3:
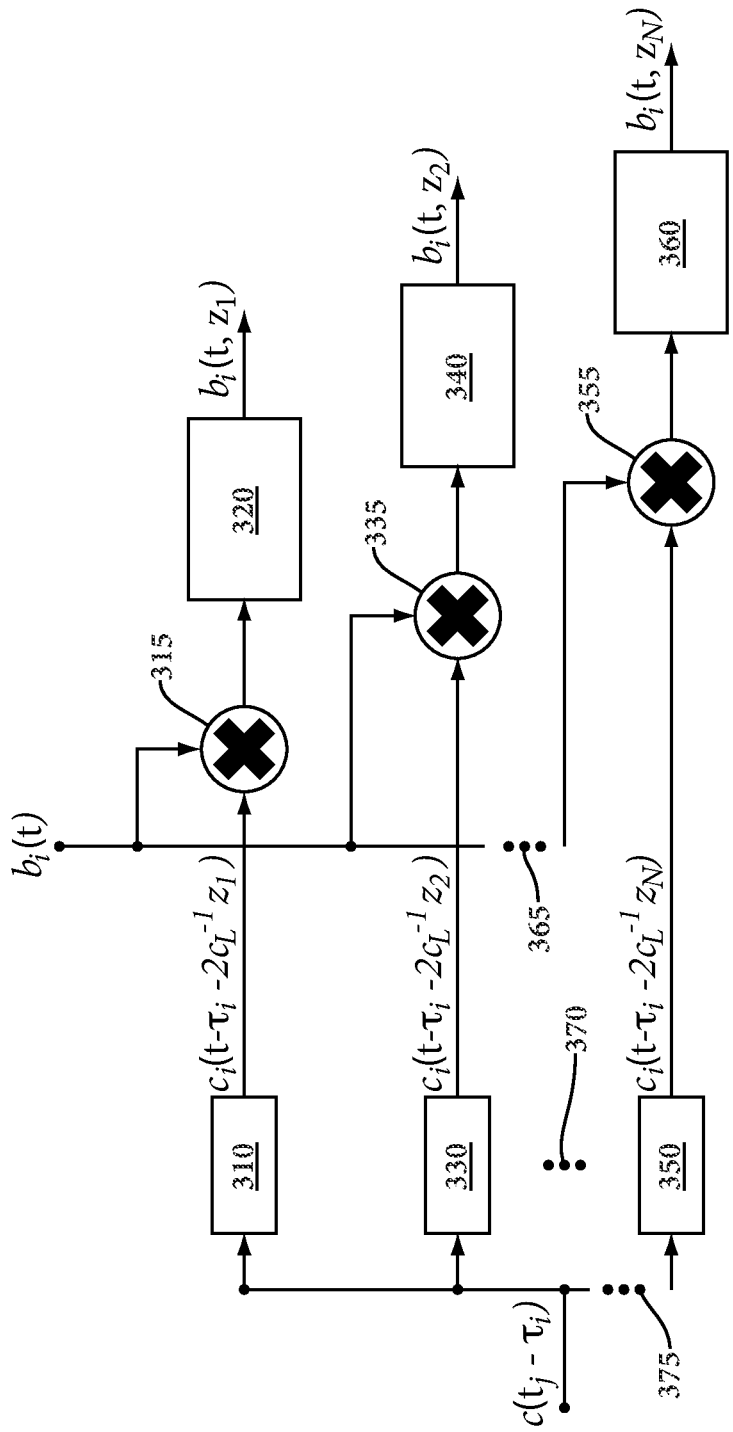
FIG. 3 illustrates a more detailed view of the decoder/despreader of each demodulator.

FIG. 3 displays the decoding scheme where, in order to obtain the frequency-modulated signal for each region of the fiber, a given coding sequence is delayed via delayers 310,330,350 by the time it takes for the optic signal to travel to the measured region and back. Notice that the code might have another delay, related to a relative delay applied in each code, which allows a slightly different region of the fiber to be sensed by each code. These signals are mixed in mixers 315, 335, and 355 and the result is then filtered in 320,340, 360 so to remove the influence of the other codes and of other regions of the fiber. A number of M such decoders should be employed in this proposal.

Figure 4:
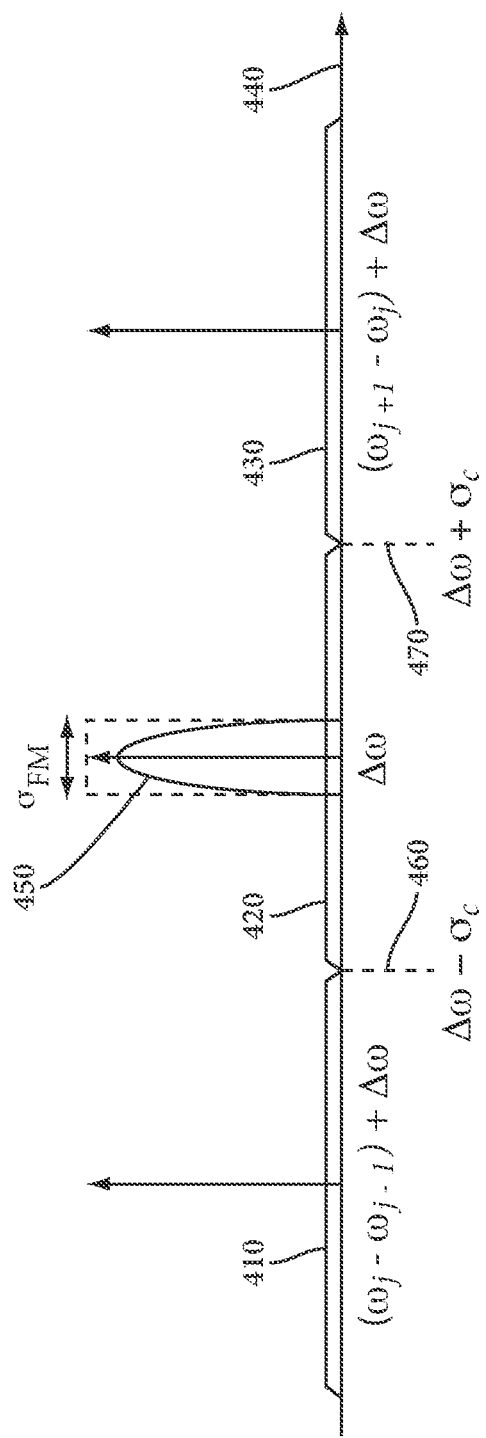
FIG. 4 illustrates a depiction of how the decoded spectrum should look before the filter is applied.

FIG. 4 depicts how the spectrum of the decoded signal, before the pass-band (or low-pass filter, in the case of homodyne detection) is applied for a single code and carrier frequency. In the diagram, three frequency components are shown, the center one at $\Delta\omega$ (450) and two neighboring components from different carrier frequencies. The optimum separation between carrier frequencies can be understood directly from this figure, where the wanted frequency-modulated pressure signal is depicted around $\Delta\omega$ frequency, and the information from different regions that were spread by the code is shown as the light grey background in 410,420,430. Ideally, the spread information from neighboring carrier frequencies should not overlap in frequency with the information from the current carrier frequency. One should bear in mind, however, that because the codes are orthogonal, the proposed system still works even if they overlap. The filter that removes the information from other regions and other codes is shown in the figure as the dashed box around the frequency-modulated pressure signal.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

The invention claimed is:

1. A system for monitoring regions of interest for occurrences that generate acoustic perturbations, comprising:
   a. an optical fiber span positioned into a region of interest;
   b. a light source for generating a continuous optical signal of a specified frequency;
   c. a frequency modulator for providing a number of shifted frequencies to produce multiple optical signals from the continuous optical signal, each having a unique frequency;
   d. a binary code sequence generator driven by a master clock for generating multiple pseudorandom binary codes, wherein the multiple pseudorandom binary codes are selected to minimize cross-correlation between the multiple pseudorandom binary codes;
   e. multiple optical modulators having first and second ports for receiving the continuous optical signal from the light source and the multiple pseudorandom binary codes from the binary code sequence generator to produce multiple modulated light signals; and
   f. an optical circulator/coupler to combine the multiple modulated light signals from the multiple optical modulators and pass the combined multiple modulated light signals into the optical fiber span positioned into the region of interest, and to receive returned backscattered Rayleigh signals from the optical fiber span positioned in to the region of interest, wherein the returned backscattered Rayleigh signals are directed to a detector system by the optical circulator/coupler;
   g. wherein the detector system comprises:
      i. a series of demodulators, each of which corresponds to one of the multiple optical modulators for transforming the optical signal from each corresponding optical modulator into an electronic signal and extracting phase information;
      ii. a phase differencer, for receiving the electronic signals from the series of demodulators so that the phase information sensed by each code from each region can be combined to obtain pressure signals corresponding to pressure impinging on a determined length of the optical fiber span; and iii. a processor to detect coherent Rayleigh noise generated by the optical fiber span positioned in the region of interest to identify acoustic perturbations in the region of interest.

2. The system for monitoring regions of interest for occurrences that generate acoustic perturbations of claim 1, wherein the light source for generating a continuous optical signal of a specific frequency is a laser.

3. The system for monitoring regions of interest for occurrences that generate acoustic perturbations of claim 1, wherein each of the series of demodulators in the detector system comprises:
   a. a heterodyne or homodyne demodulator;
   b. a decoder; and
   c. an FM demodulator.

4. The system for monitoring regions of interest for occurrences that generate acoustic perturbations of claim 3 wherein a demodulator of the series of demodulators is a heterodyne demodulator and the decoder utilizes band-pass filtering.

5. The system for monitoring regions of interest for occurrences that generate acoustic perturbations of claim 3 wherein a demodulator of the series of demodulators is a homodyne demodulator and the decoder utilizes low-pass filtering.

6. The system for monitoring regions of interest for occurrences that generate acoustic perturbations of claim 3 wherein the region of interest can include a subsurface wellbore, an oil reservoir, or a pipeline.

7. The system for monitoring regions of interest for occurrences that generate acoustic perturbations of claim 3 wherein the region of interest can include structures such as subsea umbilical's or risers.

8. The system for monitoring regions of interest for occurrences that generate acoustic perturbations of claim 3 wherein the region of interest can include perimeters encircling high security areas.

9. A method for monitoring regions of interest for occurrences that generate acoustic perturbations, comprising:
   deploying a fiber optic cable into a region of interest;
   transmitting a continuous wave light signal to a frequency modulator;
   modulating a frequency of the continuous wave light signal to generate a finite number of optical signals, each having a unique frequency;
   transmitting each of the finite number of optical signals to a corresponding number of optical modulators along with bipolar pseudorandom binary sequence codes, each of which is delayed relative to a reference coding sequence, wherein the bipolar pseudorandom binary sequence codes are selected to minimize cross-correlation between the bipolar pseudorandom binary sequence codes, wherein the optical modulators generate modulated optical signals;
   combining each of the modulated optical signals in an optical circulator/coupler;
   transmitting the combined optical signals from the optical circulator/coupler into the fiber optic cable deployed in the region of interest;
   collecting and separating backscattered Rayleigh signals from the deployed fiber optic cable, and transmitting the separated backscattered Rayleigh signals to a series of demodulators corresponding to the number of optical modulators, transforming the separated signals into electronic signals, de-coding the electronic signals by their appropriate codes, and extracting phase information; and
   transmitting the electronic signals to a phase differencer so that the phase information sensed by each code from each region can be combined to obtain pressure signals representing pressure impinging on a determined length of the fiber optical cable;
   identifying acoustic perturbations from locations in the region of interest based on the separated backscattered Rayleigh signals.

10. The method for monitoring regions of interest for occurrences that generate acoustic perturbations of claim 9 wherein the bipolar pseudorandom binary sequence codes are binary sequences of ones and negative ones.

11. The method for monitoring regions of interest for occurrences that generate acoustic perturbations of claim 9 wherein the occurrences are generated by impacts of sand grains.

12. The method for monitoring regions of interest for occurrences that generate acoustic perturbations of claim 9 wherein the occurrences are generated by proppant noise in hydraulic fracturing operations.

13. The method for monitoring regions of interest for occurrences that generate acoustic perturbations of claim 9 wherein the occurrences are generated by high frequency wellbore leaks.

14. The method for monitoring regions of interest for occurrences that generate acoustic perturbations of claim 9 wherein the occurrences are generated by wireline sonic logging.

15. The method for monitoring regions of interest for occurrences that generate acoustic perturbations of claim 9 wherein the occurrences are generated by inter-zone leaks in wellbores.

16. The method for monitoring regions of interest for occurrences that generate acoustic perturbations of claim 9 wherein the occurrences are generated by flow cavitation.

17. The method for monitoring regions of interest for occurrences that generate acoustic perturbations of claim 9 wherein the occurrences are generated by flow vortex shedding.

18. The method for monitoring regions of interest for occurrences that generate acoustic perturbations of claim 9 wherein the occurrences are generated by a particular flow regime.

19. The method for monitoring regions of interest for occurrences that generate acoustic perturbations of claim 9 wherein the occurrences are generated by a particular flow rate.

20. The method for monitoring regions of interest for occurrences that generate acoustic perturbations of claim 9 wherein the occurrences are generated by a particular fluid fraction.

21. The method for monitoring regions of interest for occurrences that generate acoustic perturbations of claim 9 wherein the occurrences are part of an active ultrasonic flow monitoring system.

* * * * *